United States Patent
Young

(12) 
(10) Patent No.: US 6,274,748 B1
(45) Date of Patent: Aug. 14, 2001

(54) PROCESS FOR THE MANUFACTURE OF COMPOUNDS CONTAINING A FATTY ACID MOIETY

(75) Inventor: John M. Young, Redwood City, CA (US)

(73) Assignee: Zenith Cosmetic Technologies LLC, Aurora, CO (US)

( * ) Notice: Subject to any disclaimer, the term of this patent is extended or adjusted under 35 U.S.C. 154(b) by 0 days.

(21) Appl. No.: 09/548,980

(22) Filed: Apr. 14, 2000

Related U.S. Application Data

(60) Provisional application No. 60/129,269, filed on Apr. 14, 1999.

(51) Int. Cl.[7] ................................................. C07C 231/00
(52) U.S. Cl. .................................................. 554/69
(58) Field of Search ................................. 554/69

(56) References Cited

U.S. PATENT DOCUMENTS

| | | | | |
|---|---|---|---|---|
| 4,481,150 | * | 11/1984 | Ishii et al. | 260/513 |
| 4,582,651 | * | 4/1986 | Ishii et al. | 260/513 |

* cited by examiner

*Primary Examiner*—Deborah D. Carr
(74) *Attorney, Agent, or Firm*—Kilpatrick Stockton LLP

(57) ABSTRACT

The invention relates to a process for making compounds having fatty acid moieties by reacting a fatty acid with a (hydroxyalkyl)amino alkane acid or a (hydroxyalkyl)amine and an aqueous base followed by heating the reaction mixture. The process is particularly useful for the formation of di-fatty acid esters from BES, and tri-fatty acid esters from TES. The reaction parameters can be adjusted to produce useful additional products of the TES-trioleate, including fatty acid amides of mono-, di- and tri-oleoyl-TES.

2 Claims, No Drawings

PROCESS FOR THE MANUFACTURE OF COMPOUNDS CONTAINING A FATTY ACID MOIETY

CONTINUING DATA

This application claims priority to U.S. Provisional Application Ser. No. 60/129,269, filed Apr. 14, 1999.

FIELD OF THE INVENTION

The invention relates generally to a process of reacting acids and alcohols. More particularly the invention relates to the reaction of a water-insoluble fatty acid with a water-soluble (hydroxyalkyl)amino alkane acid or (hydroxyalkyl) amine.

BACKGROUND OF THE INVENTION

Current methods for preparing fatty acid esters include the reaction of fatty acid with an alcohol under acid catalytic conditions. The reaction requires the removal of water to drive the equilibrium of the reaction in the desired direction. Additionally, some polyhydroxy compounds which are crystalline or have high melting points, such as tris (hydroxymethyl)methylamino ethanesulfonic acid (TES) and bis(hydroxyethyl)amino ethanesulfonic acid (BES) do not mix readily with fatty acids. TES and BES will dissolve in aqueous acid, but the resulting solution is not miscible with liquid fatty acid, and the reaction does not readily proceed. Therefore, this reaction is of limited use in forming fatty derivatives of such water soluble compounds.

Alternatively, esters of fatty acids can be prepared by reacting a fatty acid halide with a polyhydroxy compound in acetonitrile. For example, the tri-oleoyl ester of TES may be prepared by reacting oleoyl chloride and TES in acetonitrile. However, oleoyl chloride is not readily available in the quantities or purity necessary for commercial production of such esters. While it is possible to generate the oleoyl chloride in situ from relatively pure oleic acid and sulfuryl chloride, or other agents suitable for generating an acid chloride from a fatty acid, the process has not been demonstrated on a commercial scale.

SUMMARY OF THE INVENTION

The present invention relates generally to the reaction of a fatty acid and a (hydroxyalkyl)amino alkane acid or a (hydroxyalkyl) amine to form a compound having multiple ester groups and, under appropriate conditions, an amide group. In part, the present invention relates to a process for manufacturing compounds which is more economical than methods previously known in the art. This process is advantageous over the known processes because it does not require the use of a water-insoluble fatty acid chloride which is not readily available in commercial quantities. Additionally, the process of the present invention does not require the use of a solvent, such as acetonitrile, capable of solubilizing both lipids and water-soluble substances.

In a preferred embodiment, the present invention provides a process which employs a water-insoluble fatty acid and a (hydroxyalkyl)amino alkane acid or a (hydroxyalkyl) amine, to produce compounds, containing fatty acid ester moieties and/or fatty acid amide moieties, which have cytoprotective properties. For example, the compounds have antioxidant, emollient, skin penetration enhancing and/or anti-inflammatory properties and, therefore, are useful as pharmaceuticals and cosmetics.

Accordingly, it is an object of the present invention to provide a process which overcomes problems associated with other methods which use oleoyl chloride or other fatty acid chlorides which are not readily available in the bulk and purity to produce the desired compounds in commercially viable quantities.

It is another object of the present invention to provide a process which eliminates the problems associated with the use of acetonitrile or similar solvents, thereby providing a process which is subject to less stringent regulatory controls with respect to solvent residues and solvent disposal.

Yet another object of the present invention is to provide a process which is more economical than current methods for the production of fatty acid derivatives of BES and TES, and other water-soluble (hydroxyalkyl)amino alkane acids or (hydroxyalkyl)amines.

It is a further object of the present invention to provide a process which allows for more control, milder conditions, and less manipulation than current methods while producing a useful product.

Still another object of the present invention is to provide a process which is more versatile, allowing for the production of several different products based upon the particular reactants and reaction conditions.

A further object of the present invention is to produce compounds containing fatty acid ester and amide moieties by reacting a fatty acid with a (hydroxyalkyl)amino alkane acid or a (hydroxyalkyl) amine in the presence of an aqueous base.

Yet another object of the present invention is to provide a process for the production of TES-trioleate and TES-trioleate monoleoylamide by reacting TES with oleic acid.

Another object of the present invention to provide a process for the production of BES-dioleate and BES-monooleate by reacting BES with oleic acid.

It is an object of the present invention to provide a means of bringing the reactants of the process together in a homogeneous mixture so that they may more readily and effectively combine to produce the desired product.

These and other objects, features, and advantages of the present invention will become apparent after a review of the following detailed description.

DETAILED DESCRIPTION

Generally, the process of the present invention comprises mixing one or more fatty acids with a (hydroxyalkyl)amino alkane acid or a (hydroxyalkyl) amine to form compounds containing multiple fatty acid ester groups. More particularly, the process comprises mixing one or more water-insoluble fatty acids with a water-soluble (hydroxyalkyl)amino alkane acid or a (hydroxyalkyl) amine and an aqueous base to form a homogeneous mixture in which the water-insoluble fatty acid and the water-soluble (hydroxyalkyl)amino alkane acid or (hydroxyalkyl) amine may readily undergo chemical reaction to produce compounds containing multiple fatty acid ester groups, and, under certain circumstances, a fatty acid amide group.

Preferred fatty acids are those which are water-insoluble, especially unsaturated fatty acids. Due to the tendency of unsaturated fatty acids to oxidize at temperatures over 80° C., it is necessary to protect such compounds from atmospheric oxygen when temperatures above 80° C. are employed. This may be accomplished, for example, by the use of an inert gas to displace oxygen, such as argon or nitrogen, or other non-oxidizing gases such as carbon dioxide.

Fatty acids which are useful in the present invention include, but are not limited to, those having the following structural formula:

$$HO-\overset{O}{\underset{\|}{C}}-(CH_2)_n-(CH=CH-CH_2)_m-(CH_2)_x-CH_3$$

wherein n is an integer from 1 to 18, m is an integer from 0 to 4, and x is an integer from 0 to 12. Optionally, one or both of the hydrogen atoms of one or more of the —(CH$_2$)— groups may be replaced by a bond. Thus, the fatty acids of the present invention may be fully saturated or may contain unsaturations in the form of one or more double or triple bonds between any of the carbon atoms. Further, any of the —(CH$_2$)— groups can be exchanged for an —O—, —S—, or —N— atom, resulting in an ether, thioether, or amine containing fatty acid.

Those fatty acids useful in the present invention are either known in the art or can be prepared by conventional methods. The number and positions of the unsaturations may be varied by methods known in the art. Preferred unsaturated fatty acids include, but are not limited to, oleic acid, linoleic acid, linolenic acid, palmitoleic acid, and arachidonic acid, with oleic acid being especially preferred. Preferred saturated fatty acids include, but are not limited to, lauric acid, myristic acid, palmitic acid, stearic acid and eicosanoic acid. It is understood that fatty acids available commercially in large quantities may contain mixtures of these and other fatty acids. For example, oleic acid available in bulk is typically 75%–90% oleic acid with varying amounts of mono-unsaturated, di-unsaturated and tri-unsaturated fatty acids, as well as saturated fatty acids.

Any (hydroxyalkyl)amino alkane acid or (hydroxyalkyl) amine may be employed in the present invention. However, the invention is particularly useful for (hydroxyalkyl)amino alkane acids or (hydroxyalkyl)amines which are lipid-insoluble, crystalline, or solid. Some of these compounds include, but are not limited to those having the following formula:

$$[(HO\text{-}alkane)]_x N[H]_y-CH_2(CHR)_z-A$$

wherein x is 1 or 2, y is 0 or 1, and x+y=2; z is 0, 1, 2, or 3. A is an acid and preferred acids for A include, but are not limited to, COOH, PO$_3$H, and SO$_3$H. R is independently selected from H and OH. [(HO-alkane)] is preferably [HOCH$_2$CH$_2$] or [(HOCH$_2$)$_d$(CH$_3$)$_e$C] wherein d is 1, 2, or 3; e is 0, 1, or 2; and d+e=3.

Preferred compounds include the following:

| | |
|---|---|
| (HOCH$_2$)$_3$CN*H CH$_2$CH$_2$CH$_2$SO$_3$H | TAPS |
| (HOCH$_2$CH$_2$)$_2$NCH$_2$CH$_2$CH$_2$SO$_3$H | Not named |
| (HOCH$_2$)$_3$CN*H CH$_2$CH$_2$CH$_2$CH$_2$SO$_3$H | TABS |
| (HOCH$_2$CH$_2$)$_2$NCH$_2$CH$_2$CH$_2$CH$_2$SO$_3$H | Not named |
| (HOCH$_2$)$_3$CN*HCH$_2$$\overset{OH}{\underset{|}{C}}$HCH$_2$SO$_3$H | TAPSO |
| (HOCH$_2$CH$_2$)$_2$NCH$_2$$\overset{OH}{\underset{|}{C}}$HCH$_2$SO$_3$H | DIPSO |
| (HOCH$_2$)$_3$CN*HCH$_2$CO$_2$H | TRICINE |
| (HOCH$_2$CH$_2$)$_2$NCH$_2$CO$_2$H | BICINE |
| HOCH$_2$-C(CH$_3$)(CH$_3$)-N*HCH$_2$$\overset{OH}{\underset{|}{C}}$HCH$_2$SO$_3$H | AMPSO |
| HOCH$_2$CH$_2$N(piperazine)NCH$_2$CH$_2$SO$_3$H | HEPES |
| HOCH$_2$CH$_2$N(piperazine)NCH$_2$CH$_2$CH$_2$SO$_3$H | EPPS |
| HOCH$_2$CH$_2$NN(piperazine)NCH$_2$CH$_2$CCH$_2$CH$_2$SO$_3$H | HEPBS |
| HOCH$_2$CH$_2$N(piperazine)NCH$_2$$\overset{OH}{\underset{|}{C}}$HCH$_2$SO$_3$H | HEPPSO |
| C$_6$H$_{11}$N*HCH$_2$$\overset{}{\underset{OH}{C}}$HCH$_2$SO$_3$H | CAPSO |
| O(morpholine)NCH$_2$$\overset{}{\underset{OH}{C}}$HCH$_2$SO$_3$H | MOPSO |
| HO$_3$SCH$_2$$\overset{}{\underset{OH}{C}}$HCH$_2$N(piperazine)NCH$_2$$\overset{}{\underset{OH}{C}}$HCH$_2$SO$_3$H | POPSO |

The asterisk (*) adjacent to nitrogen (N) in the structures presented above indicates a reactive nitrogen. The following compounds, TES and BES, are most preferred:

| | |
|---|---|
| (HOCH$_2$)$_3$CNH CH$_2$CH$_2$SO$_3$H | TES |
| (HOCH$_2$CH$_2$)$_2$NCH$_2$CH$_2$SO$_3$H | BES | and, by extension, like structures wherein —SO$_3$H is replaced by other acid moieties, including but not limited to CO$_2$H and PO$_3$H.

Preferred (hydroxyalkyl)amino alkane acids and (hydroxyalkyl)amines useful in the present invention, include but are not limited to compounds known in the art as Good buffers, which are currently available from Sigma Chemical Co., St. Louis, Mo. and other sources. Suitable (hydroxyalkyl)amino alkane acid buffers or (hydroxyalkyl) amines include, but are not limited to the following: N,N-bis[2-hydroxyethyl]-2-aminoethanesulfonic acid (BES), N,N-bis[2-hydroxyethyl]glycine (BICINE); N-[2-hydroxyethyl]piperazine-N'-[3-propanesulfonic acid] (EPPS); N-[2-hydroxyethyl]piperazine-N'-[4- butanesulfonic acid] (HEPES); N-tris[hydroxymethyl] methyl-3-aminopropanesulfonic acid (TAPS); N-tris [hydroxymethyl]methyl-2-aminoethanesulfonic acid (TES); and N-tris[hydroxymethyl]methylglycine (TRICINE), and salts thereof. Preferred buffers include TES and BES. Other acceptable buffers are listed in the biological buffers section of the 1999 Sigma catalog, at pages 1910–1917, which are hereby incorporated by reference in their entirety. These include AMPSO, CAPSO, DIPSO, HEPBS, HEPPSO, MOPSO, POPSO, TABS, TAPS, TAPSO, and salts thereof.

In one embodiment of the present invention, a slurry of a fatty acid and a (hydroxyalkyl)amino alkane acid or a (hydroxyalkyl) amine is agitated vigorously at temperatures between approximately 80° C. and 100° C. If the fatty acid is a solid at room temperature, it may be necessary to melt it before forming a slurry with the (hydroxyalkyl)amino alkane acid or (hydroxyalkyl)amine. Next, a solution of an aqueous base is added to the heated slurry under agitation, and the temperature is gradually raised to approximately 120° C. with the evolution of excess water as steam. The quantity of aqueous base added is an amount sufficient to dissolve the (hydroxyalkyl)amino alkane acid or (hydroxyalkyl)amine and produce a sufficient amount of fatty acid salt to permit homogenization of the mixture as the temperature is raised and the excess water is driven off. The homogeneous mixture is then heated to temperatures between approximately 130° C. and approximately 170° C., more particularly between approximately 140° C. and approximately 170° C., and preferably between approximately 145° C. and approximately 160° C. under an inert atmosphere to exclude oxygen from the reaction mixture, resulting in the desired reaction between the (hydroxyalkyl) amino alkane acid or (hydroxyalkyl)amine and the fatty acid.

In another embodiment, the (hydroxyalkyl)amino alkane acid or the (hydroxyalkyl) amine can first be dissolved in the aqueous base to form a mixture. This mixture is then added to the fatty acid slurry which is preheated to temperatures between approximately 80° C. and approximately 100° C. The resulting combination is thoroughly mixed to produce a homogenous mixture. The homogeneous mixture is then heated to temperatures between approximately 130° C. and approximately 170° C., resulting in the desired reaction between the (hydroxyalkyl)amino alkane acid or the (hydroxyalkyl) amine and the fatty acid, more particularly between approximately 140° C. and approximately 170° C., and preferably between approximately 145° C. and approximately 160° C. under an inert atmosphere to exclude oxygen from the reaction mixture, resulting in the desired reaction between the (hydroxyalkyl)amino alkane acid or (hydroxyalkyl)amine and the fatty acid.

In yet another embodiment, the aqueous base can be added to the fatty acid slurry while heating the slurry to temperatures between about 80° C. and 100° C. The (hydroxyalkyl)amino alkane acid or (hydroxyalkyl)amine is then added to the mixture. The resulting combination is thoroughly mixed to produce a homogeneous mixture. The homogeneous mixture is then heated to temperatures between approximately 130° C. and approximately 170° C. to produce the desired reaction between the (hydroxyalkyl) amino alkane acid or (hydroxyalkyl)amine and the fatty acid more particularly between approximately 140° C. and approximately 170° C., and preferably between approximately 145° C. and approximately 160° C. under an inert atmosphere to exclude oxygen from the reaction mixture, resulting in the desired reaction between the (hydroxyalkyl) amino alkane acid or (hydroxyalkyl)amine and the fatty acid.

While each reaction requires some variation in conditions depending upon the exact reactants employed, the basic principle involves the addition of an aqueous base in amounts sufficient to produce the corresponding salt of the fatty acid which is necessary to result in a homogeneous reaction mixture. The reaction also requires the addition of water sufficient to dissolve the (hydroxyalkyl)amino alkane acid or (hydroxyalkyl)amine; however, excess water is not desirable since it must be boiled away before the mixture can become homogeneous. The water is advantageously supplied by the use of an aqueous base, or by the addition of water as necessary.

The process of the invention is generally described as follows. In the first step of the process, a fatty acid and a (hydroxyalkyl)amino alkane acid or (hydroxyalkyl)amine are heated and agitated at temperatures which will result in the formation of a mixture. The temperature at this step is such that the fatty acid and (hydroxyalkyl)amino alkane acid or (hydroxyalkyl)amine do not react chemically. Generally, temperatures between approximately 70° C. and approximately 105° C. are sufficient to produce the mixture, preferred temperatures are between about 90° C. and 105° C. The mixture is continually agitated during this step. The amount of fatty acid employed in the invention depends upon the number of reactive hydroxyl groups in the (hydroxyalkyl)amino alkane acid or (hydroxyalkyl)amine and is generally at least 1 mole of fatty acid:1 mole of hydroxyalkyl groups within the (hydroxyalkyl)amino alkane acid or (hydroxyalkyl)amine. For example, if a (hydroxyalkyl)amino alkane or (hydroxyalkyl)amine contains 3 hydroxyalkyl groups, then 3 moles of fatty acid should be employed for every mole of the (hydroxyalkyl) amino acid or (hydroxyalkyl)amine.

Once the mixture is formed, an aqueous base is added to the mixture, dropwise or in a thin stream, while the mixture is maintained in a state of vigorous agitation or mixing. The base reacts with the fatty acid to form a salt, permitting intimate contact between the fatty acid and the (hydroxyalkyl)amino alkane acid or (hydroxyalkyl)amine. This reaction is exothermic and may result in a slight rise in the temperature of the mixture. The base also provides sufficient water to dissolve the (hydroxyalkyl)amino alkane acid or (hydroxyalkyl)amine. While any base may be used, the preferred bases are sodium hydroxide, potassium hydroxide, ammonium hydroxide and lithium hydroxide.

The concentration of base employed is that which allows homogeneity of the reactants without resulting in an excess of water. The preferred concentration of the base is a 10 normal (N) solution. The amount of base employed in the invention is that which produces sufficient quantity of fatty acid salt to form a homogeneous mixture with the (hydroxyalkyl)amino alkane acid or (hydroxyalkyl)amine without solidification of the salt when water is driven from the reaction mixture. For example, when the fatty acid is oleic acid and the base is aqueous sodium hydroxide, the molar ratio of base to fatty acid should be approximately 1:3 to 1.2:3. A lower ratio may result in insufficient sodium oleate to produce a homogeneous mixture when water is driven from the reaction mixture. A higher ratio results in excess sodium oleate (melting point 232° C. to 235° C.) which will solidify in the mixture also preventing formation of a homogeneous solution as water is driven off. One of ordinary skill in the art may readily determine the respective molar ratios of base to fatty acid depending upon the particular components employed.

The base is preferably added to the mixture dropwise or in a stream. At the conclusion of the addition of the base there are two phases. One phase consists of a solution of fatty acid and fatty acid salt, and the second phase consists of an aqueous solution of the (hydroxyalkyl)amino alkane acid or (hydroxyalkyl)amine. The fatty acid salt serves as a detergent to homogenize the mixture. At this stage the temperature of the vigorously stirred mixture is rapidly elevated to a range of approximately 140° C. to approximately 170° C. under an inert gas atmosphere. Water vapor is removed either in an inert gas stream, by the application of vacuum, or both. When an adequate amount of water has been removed, the two phases merge forming a homogeneous solution between approximately 110° C.–125° C.

The mixture is then heated to temperatures above about 140° C. At such temperatures the fatty acid reacts with the (hydroxyalkyl)amino alkane acid or (hydroxyalkyl)amine to produce the desired chemically bonded product. This reaction occurs readily between about 140° C. and about 185° C. The rate of the chemical reaction increases with increasing temperature. Temperatures above about 185° C. are not preferred because such temperatures may cause the formation of colored products (from yellow to orange to red with increasing temperature). Higher temperatures may also result in the formation of numerous by-products that are difficult to separate from the reaction mixture.

As water is driven off rapidly the (hydroxyalkyl)amino alkane acid or (hydroxyalkyl)amine may crystallize out of aqueous solution as a very finely divided precipitate but this will re-dissolve and react as the temperature is raised to 140° C.–170° C. The resulting homogeneous solution contains fatty acid, fatty acid salt, (hydroxyalkyl)amino alkane acid or (hydroxyalkyl)amine, and residual water.

Since oxidation of the unsaturated fatty acids occurs at temperatures above 80° C., oxygen must be excluded from the reaction mixture. This may be accomplished by conducting the reaction in an inert atmosphere, such as an atmosphere of argon or nitrogen gas.

Some features of the present invention will be illustrated in terms of the preferred reactants, oleic acid as the fatty acid, TES and BES as the (hydroxyalkyl)amino alkane acid, and sodium hydroxide as the base. It should be understood that the invention is not limited to these embodiments and may be practiced with any unsaturated fatty acid, any (hydroxyalkyl)amino alkane acid or (hydroxyalkyl)amine, and any base.

When TES is reacted with oleic acid, the product formed is 2-[Tris(oleoyloxymethyl)methylamino]-1-ethanesulfonic acid, also called PX-13. The reaction scheme is as follows:

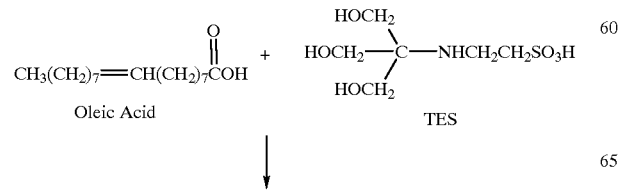

Oleic Acid  TES

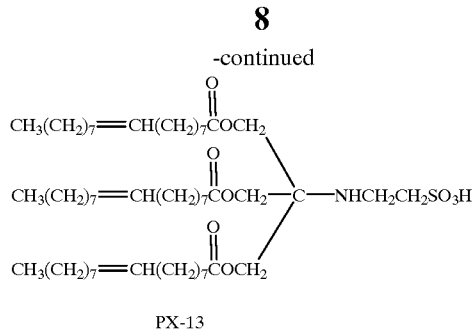

PX-13

When reaction temperatures below about 140° C. are employed, PX-13 is the predominant product. At higher temperatures, for example those between about 150° C. and about 180° C., the PX-13 produced undergoes further reaction with oleic acid to provide an amide. This product may be present in the form of several isomers as shown below:

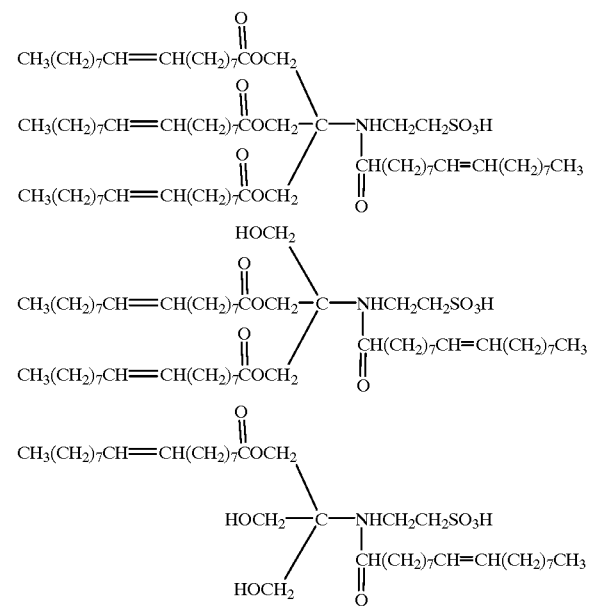

While not being bound to any particular mechanism, it is believed that these products are formed by the transfer of one of the oleoyl groups from the oxymethyl group to the secondary amino group to form an amide. At temperatures of about 160° C. or greater, PX-13 is transformed almost entirely into the rearrangement addition product.

When BES is reacted with oleic acid, the product formed is 2-[N,N-Bis(2-oleoyloxyethyl)amino]-1-ethanesulfonic acid, also called PX-18. The reaction scheme is as follows:

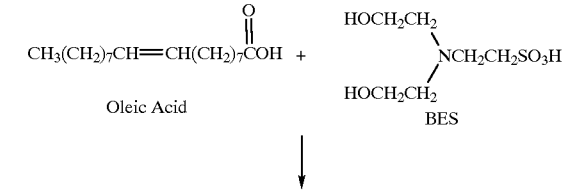

Oleic Acid  BES

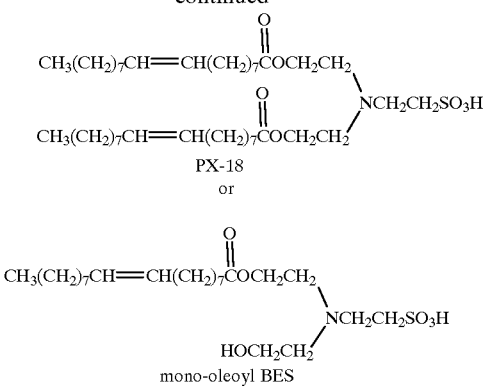

PX-18 or mono-oleoyl BES

Unlike the formation of PX-13, no internal rearrangement occurs in the above reaction because the group formed by the nitrogen atom and the alkyl moieties attached to it is a tertiary amine which cannot form an amide linkage. Temperatures up to about 170° C. may advantageously be used to form PX-18.

This invention is further illustrated by the following examples, which are not to be construed in any way as imposing limitations upon the scope thereof. On the contrary, it is to be clearly understood that resort may be had to various other embodiments, modifications, and equivalents thereof which, after reading the description herein, may suggest themselves to those skilled in the art without departing from the spirit of the present invention.

EXAMPLE 1

85 g (0.3 moles) of oleic acid were mixed with 12 g (0.05 moles) of TES at 70° C. in a 250 ml Erlenmeyer flask into which was delivered a stream of nitrogen gas by means of a tube placed into the neck of the flask. 5 ml of 10 N (0.05 mole) NaOH were added to mixture in a thin stream over a period of 10 minutes with vigorous mixing by means of a magnetic stirring bar. During addition of NaOH, the temperature of the mixture was raised from 70° C. to 85° C. over a period of approximately 10 minutes. Further addition of 1 ml of 10 N NaOH over 10 minutes produced an apparently homogeneous mixture at a temperature of 102° C. The temperature was slowly raised over 30 minutes to approximately 130° C., whereupon a white solid was observed on the bottom of the flask. The mixture was cooled to 90° C., an additional 5 ml of 10 N NaOH was added, and the temperature was raised to 100° C., resulting in a clear, colorless homogeneous solution. Vigorous boiling and evolution of water vapor occurred while the temperature was raised to 138° C. over a period of one hour. Thin layer chromatography indicated that only a trace of TES-trioleate had been formed. The mixture was then heated to a temperature of between about 148° C. to 157° C. for 3 hours in an $N_2$ atmosphere to produce TES-trioleate (PX-13) in excess oleic acid. HPLC analysis indicated that the mixture contained 48% TES-trioleate and 6% TES-trioleate monoleoylamide.

EXAMPLE 2

169 g (0.6 moles) of oleic acid were mixed with 23 g (0.1 moles) of TES and heated to 95° C. while stirring under a nitrogen atmosphere. 20 ml (0.2 moles) of 10 N NaOH was added to the mixture over 10 minutes. The temperature of the reaction mixture was gradually raised to 148° C. over a period of 2 hours, and then maintained at a temperature of between about 148° C. and 151° C. for 6 hours. Thin layer chromatography showed the presence of TES-trioleate and TES-dioleate plus excess oleic acid. The mixture was then heated to a temperature of between about 170° C. and 180° C. in an $N_2$ atmosphere for 6.5 hours to produce the TES-trioleate monoleoylamide product. HPLC analysis of the final mixture indicated the presence of 63% oleic acid, 25% TES-trioleate monooleoylamide and 6% TES-trioleate.

EXAMPLE 3

1700 g (6 moles) of oleic acid were mixed with 230 g (1 mole) of TES in a 5 liter three-neck round bottom flask placed in a heating mantle and heated to 95° C. while stirring under a nitrogen atmosphere. 200 ml (2 moles) of 10 N NaOH was gradually added to the mixture over 30 minutes. The temperature of the reaction mixture was gradually raised to 148° C. over a period of two hours, and then maintained at a temperature of 148° C. to 151° C. for 9 hours. HPLC analysis showed the presence of TES-trioleate (55%) plus excess oleic acid.

EXAMPLE 4

225 g (0.8 moles) of oleic acid were heated with 64 g (0.3 moles) of BES at 95° C. in a 500 ml Erlenmeyer flask with vigorous mixing under a nitrogen atmosphere. 27 ml of 10 N NaOH (0.27 mole) was added dropwise to the mixture over a 10 minute period. The temperature was raised from 103° C. to 134° C. over two hours. The mixture was then heated to a temperature of between about 160° C. and 172° C. with stirring in an $N_2$ atmosphere. The mixture was stirred and heated under these conditions for 6 hours. Thin layer chromatography showed the presence of BES-dioleate (PX-18), residual oleic acid and a small amount of BES-monooleate.

All patents, publications, and abstracts cited above are incorporated herein by reference in their entirety. The above examples are intended to be demonstrative, rather than limiting, of the embodiments contemplated by the invention. It should be understood that the foregoing relates only to preferred embodiments of the present invention and that numerous modifications or alterations may be made therein without departing from the spirit and scope of the present invention as defined in the following claims.

I claim:
1. A process for synthesis of compounds containing a fatty acid moiety comprising

(1) mixing a fatty acid and either a (hydroxyalkyl)amino alkane acid or a (hydroxyalkyl)amine at a temperature between about 80° C. and about 100° C. to form a first mixture;

(2) adding an aqueous base to the first mixture to form a second mixture;

(3) heating and mixing the second mixture until homogeneous; and (4) rapidly heating the second mixture to a temperature between about 130° C. and about 170° C. to remove water and form the compound.

2. A process for synthesis of compounds containing a fatty acid moiety comprising
   (1) forming a fatty acid slurry having a temperature between about 80° C. and about 100° C.;
   (2) dissolving a (hydroxyalkyl)amino alkane acid or a (hydroxyalkyl)amine in an aqueous base to form a first mixture;
   (3) adding the first mixture formed in step (2) to the fatty acid slurry to form a second mixture;
   (4) heating and mixing the second mixture until homogeneous; and
   (5) heating the homogeneous mixture to a temperature between about 130° C. and about 170° C. while removing the water formed by the reaction.

* * * * *